(12) United States Patent
Alhrishy et al.

(10) Patent No.: US 11,308,663 B2
(45) Date of Patent: Apr. 19, 2022

(54) DIGITAL IMAGE REMAPPING

(71) Applicant: Cydar Limited, Barrington (GB)

(72) Inventors: Mazen Alhrishy, Strand (GB); Graeme Penney, Barrington (GB); Tom Carrell, Barrington (GB)

(73) Assignee: Cydar Limited, Barrington (GB)

( * ) Notice: Subject to any disclaimer, the term of this patent is extended or adjusted under 35 U.S.C. 154(b) by 572 days.

(21) Appl. No.: 15/552,349

(22) PCT Filed: Feb. 19, 2016

(86) PCT No.: PCT/EP2016/053558
§ 371 (c)(1),
(2) Date: Aug. 21, 2017

(87) PCT Pub. No.: WO2016/131957
PCT Pub. Date: Aug. 25, 2016

(65) Prior Publication Data
US 2018/0040147 A1 Feb. 8, 2018

(30) Foreign Application Priority Data

Feb. 20, 2015 (GB) .................................... 1502877

(51) Int. Cl.
*A61B 5/00* (2006.01)
*G06T 11/00* (2006.01)
(Continued)

(52) U.S. Cl.
CPC ............ *G06T 11/008* (2013.01); *A61B 5/055* (2013.01); *A61B 6/02* (2013.01); *A61B 6/032* (2013.01);
(Continued)

(58) Field of Classification Search
CPC ............ G06T 11/008; G06T 7/33; A61B 6/02; A61B 6/032; A61B 6/12; A61B 6/4085;
(Continued)

(56) References Cited

U.S. PATENT DOCUMENTS 5,274,551 A * 12/1993 Corby, Jr. ............... A61B 6/463
                                                    348/45
6,154,518 A    11/2000 Gupta
(Continued)

FOREIGN PATENT DOCUMENTS

EP    2 301 432 A1    3/2011
GB    2 390 792 A     1/2004

OTHER PUBLICATIONS

International Search Report and Written Opinion for International Application No. PCT/EP2016/053558, European Patent Office, Netherlands, dated May 31, 2016, 12 pages.

*Primary Examiner* — Joel Lamprecht
(74) *Attorney, Agent, or Firm* — Sterne, Kessler, Goldstein & Fox P.L.L.C.

(57) ABSTRACT

The present invention relates to production of 2D digital images suitable for use in medical imaging. The invention particularly relates to remapping X-ray images taken from a first viewpoint so that they present the same image as seen from a second viewpoint. Remapping is achieved by registering separate 2D images taken from the first and second viewpoints of an area with a 3D scan volume of the same region to ascertain their relative viewpoints with respect to the 3D scan volume. The image taken with respect to the first viewpoint is then remapped to yield the image as seen from the second viewpoint.

12 Claims, 7 Drawing Sheets mask image     subtracted angiography frames     DSA image (51) Int. Cl.
  *A61B 6/00* (2006.01)
  *A61B 6/12* (2006.01)
  *A61B 6/02* (2006.01)
  *G06T 7/33* (2017.01)
  *A61B 5/055* (2006.01)
  *A61B 6/03* (2006.01)
  *A61B 90/00* (2016.01)

(52) U.S. Cl.
  CPC .............. *A61B 6/12* (2013.01); *A61B 6/4085* (2013.01); *A61B 6/4441* (2013.01); *A61B 6/481* (2013.01); *A61B 6/487* (2013.01); *A61B 6/504* (2013.01); *A61B 6/5205* (2013.01); *A61B 6/5223* (2013.01); *A61B 6/5235* (2013.01); *G06T 7/33* (2017.01); *A61B 2090/367* (2016.02); *A61B 2090/376* (2016.02); *A61B 2576/00* (2013.01); *G06T 2207/10081* (2013.01); *G06T 2207/10121* (2013.01); *G06T 2207/10124* (2013.01); *G06T 2207/30101* (2013.01); *G06T 2210/41* (2013.01); *G06T 2211/404* (2013.01); *G06T 2211/421* (2013.01)

(58) Field of Classification Search
  CPC ....... A61B 6/4441; A61B 6/481; A61B 6/487; A61B 6/504; A61B 6/5205; A61B 6/5223; A61B 6/5235
  See application file for complete search history.

(56) References Cited

U.S. PATENT DOCUMENTS

| | | | |
|---|---|---|---|
| 2006/0002601 A1* | 1/2006 | Fu ................. | G06T 11/008 382/132 |
| 2006/0002615 A1* | 1/2006 | Fu ................. | A61B 6/5235 382/254 |
| 2008/0101673 A1* | 5/2008 | Fu ................. | G06K 9/32 382/128 |
| 2008/0137924 A1* | 6/2008 | Boese ............. | G06T 11/008 382/128 |
| 2009/0005668 A1* | 1/2009 | West .............. | A61B 6/466 600/407 |
| 2009/0012390 A1* | 1/2009 | Pescatore ........ | A61B 6/12 600/425 |
| 2010/0246915 A1* | 9/2010 | Yamakoshi ...... | A61B 6/032 382/131 |
| 2011/0249882 A1* | 10/2011 | Bornfleth ........ | G06T 7/33 382/132 |
| 2013/0113802 A1* | 5/2013 | Weersink ........ | G06T 15/20 345/427 |
| 2014/0328531 A1* | 11/2014 | Lee ................ | G06T 19/00 382/131 |
| 2015/0138186 A1* | 5/2015 | Carrell ........... | F24C 15/2021 345/419 |
| 2016/0163045 A1* | 6/2016 | Penney ........... | G06T 15/20 382/131 |
| 2016/0302747 A1* | 10/2016 | Averbuch ........ | A61B 34/20 |

* cited by examiner

DIGITAL IMAGE REMAPPING

The present invention relates to production of 2D digital images suitable for use in medical imaging. The invention particularly relates to remapping X-ray images taken from a first viewpoint so that they present the same image as seen from a second viewpoint.

Minimally invasive surgical procedures guided by X-ray fluoroscopy such as cardiac ablation, neuroembolization, coronary artery angioplasty, and stent placement are used in a wide range of medical specialities as they are advantageous compared to invasive surgical procedures, particularly for patients not suitable for open surgery.

Such procedures allow substantial reduction of infection risk and shorter recovery times because interventional fluoroscopy requires, comparatively, only a very small incision [1].

During fluoroscopy-guided endovascular interventions, low-dose X-ray (known as fluoroscopy screening) is used to provide guidance after inserting catheters, guide wires, or other interventional instruments into the patient's blood vessel by monitoring their movement in real-time on a set of display screens in the intervention room. However, only interventional devices and dense tissues such as bone are adequately visualized using fluoroscopy screening. Soft tissue anatomy such as the vasculature is not adequately visualized.

To enhance vasculature visualisation, iodinated contrast medium (ICM) is injected into the blood vessels, and a significantly higher X-ray dose than in standard fluoroscopy screening is employed; this technique is known as angiography screening [2]. To visualize only the contrast flow and remove background structures, a mask image is acquired before the injection of ICM and then subtracted from the subsequent angiography images yielding in a digitally subtracted angiography (DSA) image showing only the enhanced vasculature.

Figure 1:
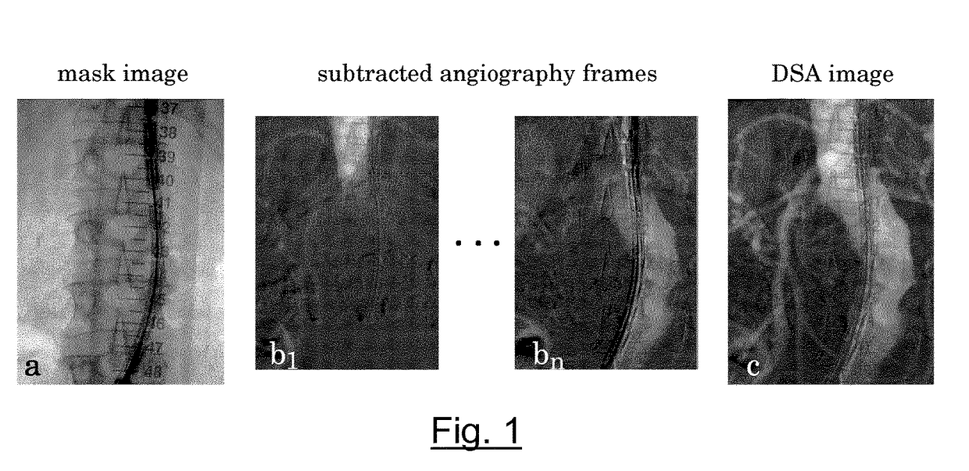
FIG. 1 Images illustrating basic digital subtraction angiography. The mask image (a) is subtracted pixel-by-pixel from all individual frames in the angiography screening ($b_1$~$b_n$). A DSA image (c) is then generated from the subtracted frames using the maximum intensity projection method.

In overview, Digital Subtraction Angiography (DSA) is a known and widely utilised technique that addresses the problem that blood vessels are not well visualized using standard fluoroscopy screening. This is because the difference in attenuation coefficients between blood and surrounding soft tissues is very small. To render the lumen of a blood vessel opaque, it is necessary to use a contrast medium with a high attenuation coefficient. One such medium is ICM, which relies on iodine for its radio-opacity. High-contrast background objects are then subtracted from the image as they obscure the lower-contrast blood vessels containing dilute iodine. Once the high-contrast structures have been removed, the subtracted image (i.e. the DSA image) can be enhanced using display windowing techniques. FIG. 1 illustrates the basic digital subtraction angiography principle which can be divided into these steps:

1. A mask image is acquired before administration of ICM (FIG. 1a).
2. ICM is injected intra-arterially and an angiography screening showing the contrast flow over time is obtained.
3. All individual frames in the angiography screening are subtracted, pixel by pixel, from the mask image to remove background high-contrast structures (FIG. $1b_1$~$b_n$).
4. The subtracted frames are then used to generate a DSA image (FIG. 1c), using the maximum intensity projection (MIP) method. In MIP, only pixels with the highest intensity values throughout the subtracted frames are projected into a single image.

If no ICM is injected, and if there is no movement of the soft tissues between taking the mask and the subsequent angiography images, the DSA image will be blank. However, in the presence of ICM, the DSA image will show the iodinated vascular structures.

However, a DSA image is only valid for this current, particular view. Once the fluoroscopy set (typically a C-arm bearing the X-ray source and detector) is moved (translated and/or rotated), the previous DSA image will not correspond to the new view. This effect is particularly pronounced because the X-rays are generated from, effectively, a point source. Therefore, during most procedures, DSA imaging is repeated, if the positional information of vascular anatomy is required after movement of the C-arm.

A further limitation of this technique is that artefacts appear due to movement between pre- and post-ICM injection images. If such cases, the mask subtraction will not totally cancel out all background structures, and motion artefacts appear in the DSA image.

ICM usage is essential during interventional procedures. However, ICM is nephrotoxic and, consequently, acute kidney injury is the main life-threatening complication of ICM use. ICM-induced acute kidney injury accounts for a significant number of cases of hospital-acquired renal failure [3], and it was reported to be the third most common cause of hospital-acquired renal failure [4]. Moreover, patients with ICM-induced acute kidney injury are at high risk of in-hospital complications including a mortality rate of 20% [5]. These risks are particularly significant for patients with renal insufficiency where ICM increases mortality rates and adverse events. This is likely to continue being the main challenge for angiography screening as chronic kidney disease and diabetes are becoming more prevalent in an ageing population [3].

Furthermore, X-ray exposure for producing DSA images was also found to contribute most of the patient radiation dose (81%) during endovascular interventions, even though ICM was used as sparingly as possible [2]. This is because angiography screening requires a significantly higher radiation dose than standard fluoroscopy screening. Added to this, the complexity of procedures is increasing. More complex procedures with longer screening times and more DSA imaging are being carried out and there are growing concerns resulting from the increasing radiation exposure to both patients and the interventional team [1]. It is expected that radiation exposures of this type will rise dramatically in the future [6]. Risks from increased radiation exposure are particularly significant for patients at high risk of radiation adverse response such as patients with a previous high-dose of radiation from an earlier treatment.

Techniques to minimize radiation exposure in the course of DSA include using 2D-3D registration algorithms to provide a 3D preoperative overlay into the 2D intraoperative fluoroscopy images during fluoroscopy-guided interventions [7]. However, intraoperative deformation can limit the quality of images obtained [8]. WO 2013/132235 describes such a 2D-3D registration technique.

This DSA remapping method utilises a well-established intensity-based 2D-3D registration algorithm [9, 10] and uses the following coordinate system:

$X_{3D}$: this defines 3D positions with respect to the X-ray fluoroscopy set (i.e. X-ray source and detector). Coordinates in $X_{3D}$ are denoted with the capital letters (X,Y,Z).

$CT_{3D}$: this defines 3D positions in the preoperative CT volume. Coordinates in $CT_{3D}$ are denoted with the small letters (x,y,z).

$I_{2D}$: this defines 2D positions in the X-ray projection image. Coordinates in $I_{2D}$ are denoted with the small letters (u,v).

Figure 3:
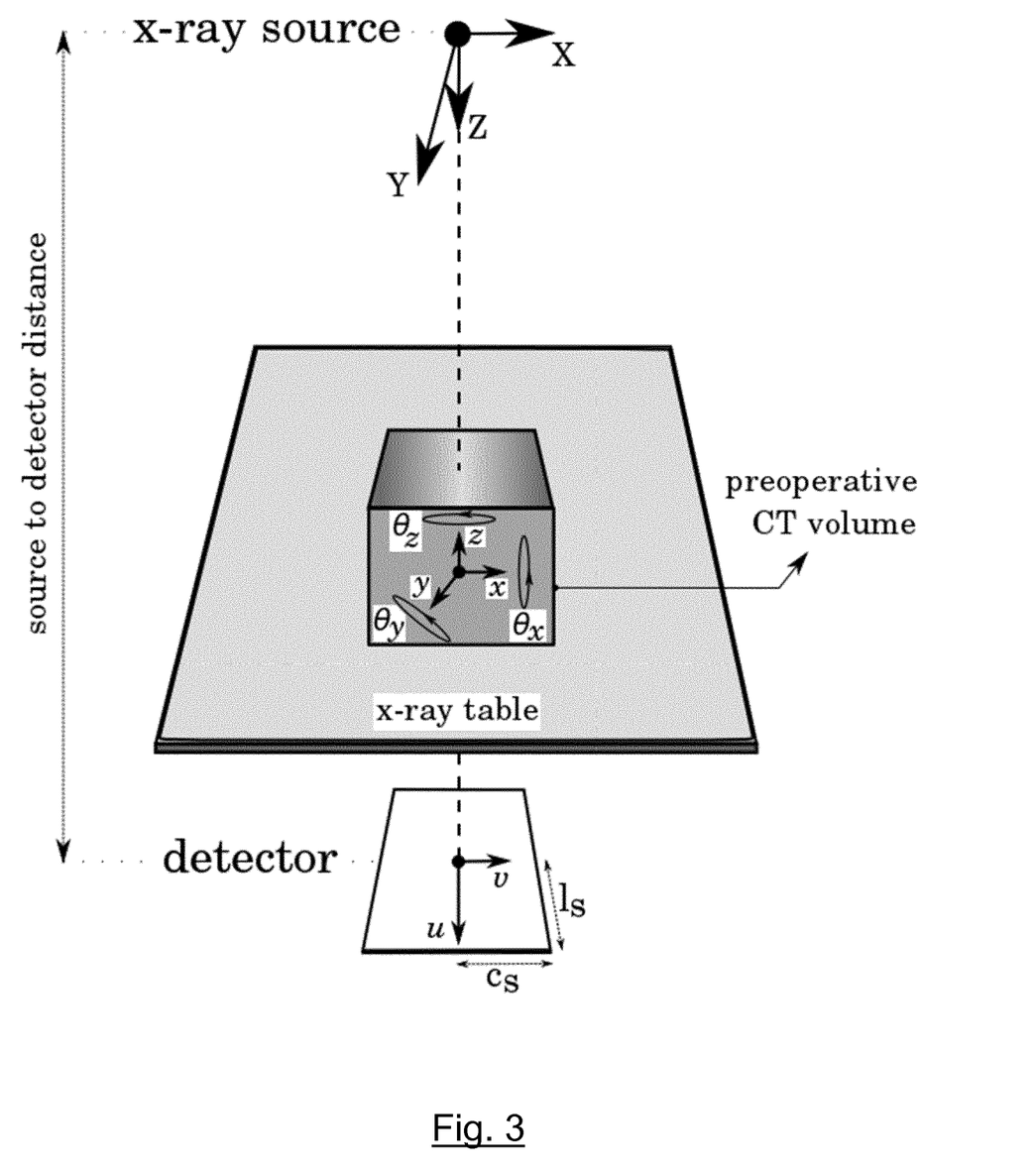
FIG. 3 The 10 degrees of freedom involved in perspective projection transformation. A preoperative CT volume is registered with the intraoperative image using a 2D-3D registration algorithm. $c_s$ and $I_s$ mark the positions of the interception between the ray projected from the X-ray source into the imaging plane. $\theta_x$, $\theta_y$ and $\theta_z$ represent the imaged object orientation, while X, Y and Z represent its position with respect to the fluoroscopy set coordinate system $X_{3D}$.

This 2D-3D registration algorithm aligns a preoperative CT volume coordinate system $CT_{3D}$ with the fluoroscopy set coordinate system $X_{3D}$ to enhance guidance during interventions, as seen in FIG. 3.

The algorithm generates digitally reconstructed radiographs (DRRs) by casting rays through an automatically segmented vertebra from the preoperative CT, and integrating voxel values above a threshold (200 HU) along each ray. DRRs can then be compared with the intraoperative fluoroscopy images using, for example, a gradient difference similarity measure [9].

FIG. 3 illustrates the 10 degrees of freedom involved in perspective projection transformation. These can be split up into 3 matrices:

A 3×4 perspective matrix $P(c_s, l_s, k_1, k_2)$, where $c_s$ and $l_s$ mark the 2D positions on the imaging plane where the normal to that plane goes through the X-ray source. $k_1$ and $k_2$ are the source to detector distance divided by the 2D image pixel sizes.

A 4×4 rotational matrix $R(\theta x, \theta y, \theta z)$, where $\theta x$, $\theta y$ and $\theta z$ represent the orientation of $CT_{3D}$ with respect to $X_{3D}$.

4×4 translation matrix $T(X,Y,Z)$, where X,Y and Z represent the position of $CT_{3D}$ with respect to $X_{3D}$.

These 3 matrices can be combined to produce a projection transformation matrix M(w) as shown in the following equation (Eqn. 1):

$$M(w)=P(c_s,l_s,k_1,k_2)R(\theta x,\theta y,\theta z)T(X,Y,Z) \quad (1)$$

Matrix M(w) relates positions (represented as homogeneous coordinates) between $CT_{3D}$ and $I_{2D}$, as shown in Eqn. (2), where $\lambda$ is a scaling factor:

$$M(w)(x,y,z,1)^T=\lambda(u,v,1)^T \quad (2)$$

Therefore, M(w) can be used to project a 3D point in $CT_{3D}$ to a 2D point in $I_{2D}$, or to transform a 2D point in $I_{2D}$ to a 3D line in $CT_{3D}$.

In addition, repeated capture of DSA images interrupts clinical work flow as for each image run the patient must be kept still and the equipment operators and other operating theatre staff must retire away from the radiation source and/or behind shielding while the patient is exposed to the radiation.

Figure 2:
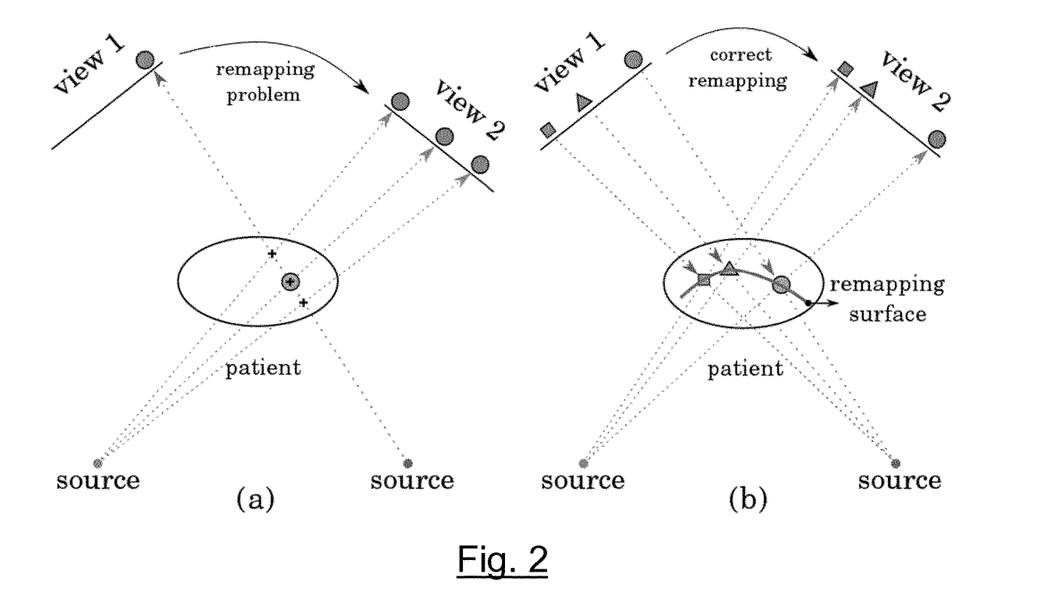
FIG. 2 Illustration of the problem of remapping projection data. (a) The 2D circle in view 1 cannot be remapped from view 1 to view 2 without knowing it's 3D position (i.e. grey circle) along the ray path for view 1. (b) If a remapping surface is known, the square, triangle and circle seen in view 1 can be correctly remapped from view 1 to view 2.

FIG. 2 illustrates the problem of remapping projection data. FIG. 2 illustrates the 2D geometry of perspective projection used in fluoroscopy imaging. In FIG. 2a the X-ray source and detector is moved around the patient from view 1 to view 2 to acquire a new 2D projection image.

FIG. 2a shows that remapping the first image into the second view direction cannot be accurately achieved using only knowledge of the relative view directions 1 and 2.

There is a need for alternative, preferably improved imaging techniques. A need addressed by specific embodiments is to provide imaging techniques that minimize the need for repeated DSA procedures and that have the concomitant benefit of reducing the volume of nephrotoxic ICM and radiation exposure, while maintaining the necessary image quality to perform complex procedures.

Accordingly, the invention provides an image generation method comprising:
a) obtaining first and second 2D images through an object to be imaged, wherein the images are from different viewpoints with respect to the object; and
b) remapping pixels of the first 2D image to generate a remapped image from the viewpoint of the second 2D image.

Preferably the method also comprises:
a) providing a 3D image data set of the object to be imaged; and
b) registering the first and second 2D images with the 3D image data set.

Preferably the method also comprises defining a remapping surface within the 3D image data set.

Disclosed herein in examples of the invention is the use of 2D-3D image registration to facilitate DSA remapping using a standard fluoroscopy system. This allows repeated ICM-free DSA and results in minimal ICM usage and reduced radiation dose, while improving the clinical workflow. Remapping is achieved by registering separate 2D images taken from the first and second viewpoints of an area with a 3D scan volume of the same region to ascertain their relative viewpoints with respect to the 3D scan volume. The image taken with respect to the first viewpoint is then remapped to yield the image as seen from the second viewpoint.

Accordingly, the invention also provides an image generation method comprising:
a) obtaining first and second 2D images through an object to be imaged, wherein the images are from different viewpoints with respect to the object;
b) providing a 3D image data set of the object to be imaged;
c) defining a remapping surface within the 3D image data set;
d) registering the first and second 2D images with the 3D image data set and determining the viewpoint of the first and second 2D images with respect to the 3D image data set;
e) remapping pixels of the first 2D image to generate an image from the viewpoint of the second 2D image by:
 i. back projecting rays from the pixels of the first 2D image and determining the points of intersection of the back projected rays with the remapping surface; and
 ii. remapping the pixels of the first 2D image corresponding to the points of intersection to generate the remapped image, whereby the pixels are remapped according to the direction of rays projected from the viewpoint of the second 2D image via the intersection points corresponding to each pixel.

Preferably the first image is a digital subtraction angiography (DSA) image.

Preferably the second 2D image is a fluoroscopy image.

The invention also provides an image generation method comprising:
a) obtaining first and second 2D images through an object to be imaged, wherein the images are from different viewpoints with respect to the object;
b) obtaining a third 2D image through an object to be imaged, wherein the third image shares the viewpoint of the first image and is aligned with the first image;
c) providing a 3D image data set of the object to be imaged;
d) defining a remapping surface within the 3D image data set;
e) registering the first and second 2D images with the 3D image data set and determining the viewpoint of the first and second 2D images with respect to the 3D image data set;

f) remapping pixels of the third 2D image to generate an image from the viewpoint of the second 2D image by:
   i. determining which pixels of the third 2D image correspond to the pixels of the first 2D image;
   ii. back projecting rays from the pixels of the first 2D image and determining the points of intersection of the back projected rays with the remapping surface; and
   iii. remapping the pixels of the third 2D image that correspond with the pixels of the first 2D image to generate the remapped image, whereby the pixels are remapped according to the direction of rays projected from the viewpoint of the second 2D image via the intersection points corresponding to each pixel.

The first 2D image may be a fluoroscopy image and the second 2D image may be a fluoroscopy image.

An advantage of using fluoroscopy images to register the position of viewpoints of the 2D images with the 3D image data set is that fluoroscopy images are relatively easily taken using a relatively low radiation dose. Furthermore, fluoroscopy can be used for real time visualisation and thus fluoroscopy can be used to find the ideal viewpoint before committing to using more involved, invasive or potentially damaging techniques, e.g. digital subtraction angiography (DSA).

Preferably, the third image is a digital subtraction angiography (DSA) image.

The invention provides the following advantages which stem from reducing the number of DSA runs that are required during an operation:

First, this method allows a reduction in the amount of iodinated contrast medium (ICM) that must be used during an operation. ICM is nephrotoxic and acute kidney injury is the main life threatening complication of ICM and was reported to be the third most common cause of hospital-acquired renal failure.

Second, this innovation in medical imaging allows a reduction in radiation exposure for both patients and operators. Digital subtraction angiography (DSA) was found to contribute for most of the patient radiation dose (81%) during endovascular intervention, because it requires a significantly higher radiation dose than standard fluoroscopy screening.

Typically, the radiation doses required to produce a standard fluoroscopy image vs as DSA image are:
   for a low dose screening fluoroscopy image approximately 0.04 $dGy.cm^2$ (deci Gray cm squared) of X-ray radiation;
   for a DSA scan approximately 50-150 $dGy.cm^2$ of radiation.

Thus, reducing the number of DSA runs very significantly reduces the exposure to X-ray radiation of both patient and operator (based on the amounts of exposure set out above this is anywhere between a 1250- and 3750-fold reduction).

A further advantage of remapping of DSA images is that the clinical workflow is improved. Taking a DSA image requires a significant amount of time during an operation because the patient must be kept still and the operators must retire to a safe distance and/or behind shielding while the DSA scan is taken. Remapping a DSA image to a more easily taken, and lower radiation, fluoroscopy image is necessarily a more efficient and clinically preferable process.

The 2D-3D registration technique described in WO 2013/132235 is particularly suitable for use in the context of this invention. This is because this technique allows:

automatic checking between images; there is no need for a technician to manually align the different images;
a large capture range for starting positions, i.e. the relative angles that each image is viewed from.

In addition, an advantage of this technique is that no non-standard equipment is required in the operating theatre. The computer that is used for the 2D-3D image registration can also be used for the remapping methods of the invention.

In addition to the advantages of fluoroscopy given above, fluoroscopy is suitable for locating and viewing parts of the anatomy that do not easily deform, e.g. bones. The quality of not deforming means that the location of these features of the anatomy can be consistently and accurately determined when surrounding softer tissues have deformed over time or during an operation.

The 3D data set can be obtained as part of the image generation in carrying out the method. It is also optional to use a 3D data set obtained otherwise, e.g. in advance.

The 3D image data set may be obtained from a computerised tomography (CT), magnetic resonance (MR) or cone beam computerised tomography scan (CBCT).

Preferably, the 3D image data set is obtained via a computerised tomography (CT) scan.

Computerised tomography is particularly suitable for use with the invention because it is suitable for accurately locating and viewing parts of the anatomy that do not easily deform, e.g. bones, as well as the surrounding softer tissue. Accuracy in locating features of anatomy that appear in 2D fluoroscopy images and 3D CT scans allows better (e.g. more accurate and more quickly achieved) 2D-3D registration of 2D fluoroscopy scans with 3D CT scans.

Other 2D-3D registration techniques are known and are suitable for use in the context of this invention. In particular the method disclosed in WO 2013/132235. Other methods include tracking of the C-arm and table after an initial registration process. The initial registration process can be carried out either automatically, semi-automatically or manually to either a 2D image or images, or a 3D image (e.g. CBCT) acquired in theatre.

The remapping surface may be any of:
   i. angled planar or multi-planar;
   ii. curved; and/or
   iii. discontinuous;
   or any combination thereof.

The remapping surface may be shaped and/or defined to substantially follow a feature in the object to be imaged.

The remapping surface being defined to substantially follow a feature in the object to be imaged is particularly advantageous when a feature to be viewed does not fall entirely within an image plane of the imaging means being used to view it. Defining the shape of the remapping surface allows all or more of an anatomical feature of interest to be viewed in a single, or reduced number of, images.

Advantageously, the remapping surface can be defined to follow a blood vessel, for example the aorta. In particular the remapping surface can be defined to follow the lumen of a blood vessel.

This is particularly advantageous as operations on three dimensional, connected networks of vessels are simplified if the need to adjust the image plane of the viewing apparatus during an operation to view the area of immediate interest is obviated by use of the invention bringing substantially all of the areas of possible interest into view/focus substantially simultaneously.

One or more features of the object to be imaged within the 3D image data set of the object to be imaged may be enhanced by the use of contrast medium.

Contrast medium is used routinely for many diagnostic CT and MR images in order to enhance the contrast and detail of images of specific features or clinical structures viewed using these techniques. Accordingly, the use of contrast medium increases the accuracy of the positional information recorded in CT and MR images. This increases the utility of the 3D image datasets when they are used in the context of the invention Contrast medium may be used to enhance images of the circulatory system, e.g. the aorta and surrounding vessels. Such images may be used for diagnosis and/or surgery planning, e.g. for endovascular aortic aneurysm procedures. The CT contrast medium may be iodinated, preferably the contrast medium is Omnipaque™ (iohexol) or Visipaque™ (iodixanol). The MR contrast medium may be gadolinium based.

A remapping surface may be defined according to the signals obtained from a contrast-enhanced CT image and defining that the remapping surface substantially follows the feature or clinical structure whose visibility is enhanced by the use of contrast medium.

Suitable contrast medium can also be used to visualise the same features or clinical structures, e.g. blood vessels using fluoroscopy in order to produce digitally subtracted angiography (DSA) images. Therefore, remapping surfaces defined in the preoperative CT based on the clinically relevant contrast-enhanced features or clinical structures can be used to remap intraoperative DSA images. Preferably the features or clinical structures are a blood vessel or vessels, e.g. the aorta.

The use of contrast medium is advantageous in the context of the present invention because it allows a user to directly locate the features or clinical structures of interest. A further advantage is that this directly derived positional information can also be directly and objectively used to define a remapping surface for the relevant features or clinical structures.

Accordingly, the invention also provides contrast medium for use in an image generation method of the invention, wherein the contrast medium is used to define a remapping surface within a 3D image data set, preferably wherein the method is for treatment or diagnosis of a human or animal body.

The invention additionally provides for the use of contrast medium in an image generation method of the invention, wherein the contrast medium is used to define a remapping surface within a 3D image data set.

Preferably, one or more of the images is a digital image. While other forms of image used with the invention, digitised images, and especially native digital images are particularly preferred.

The remapped pixels may be remapped to corresponding locations on the second 2D image.

Advantageously, remapped pixels may be used to augment all or parts of the second 2D image. Remapped pixels may be used to mark, highlight or overlay anatomical features of the second 2D image.

The intensity of the pixels may be variable.

While an image is defined by the location of pixels relative to one another the degree of brightness or intensity of signal for pixels supplies further information. This is particularly the case when a group of pixels form an intensity gradient relating to a particular feature in either or both of the original and remapped images and/or the second 2D image.

The origin of the pixels may be marked, preferably with a colour. This has the advantage in a composite image of showing the original image information (for example, from a fluoroscopy scan) overlaid or combined with image from a further remapped image (for example a DSA image) such that features of both can be viewed with reference to one another in a single image.

The invention further provides an imaging system, comprising:
a 2D imaging system arranged in use to obtain 2D images; and
a processor, arranged in use to:
a) obtain first and second 2D images through an object to be imaged, wherein the images are from different viewpoints with respect to the object;
b) remap pixels of the first 2D image to generate a remapped image from the viewpoint of the second 2D image,
optionally, arranged to operate in accordance with any of the methods described herein Preferably the imaging system also comprises a 3D image data set, and the processor of the imaging system is arranged in use to register the first and second 2D images with the 3D image data set and determine the viewpoint of the first and second 2D images with respect to the 3D image data set.

Preferably the processor of the imaging system is arranged in use to define a remapping surface within the 3D image data set.

The invention also provides an imaging system, comprising:
a 2D imaging system arranged in use to obtain 2D images to be registered with
a 3D image data set; and
a processor, arranged in use to:
a) obtain first and second 2D images through an object to be imaged, wherein the images are from different viewpoints with respect to the object;
b) define a remapping surface within the 3D image data set;
c) register the first and second 2D images with the 3D image data set and determine the viewpoint of the first and second 2D images with respect to the 3D image data set;
d) remap pixels of the first 2D image to generate an image from the viewpoint of the second 2D image by:
i. back projecting rays from the pixels of the first 2D image and determining the points of intersection of the back projected rays with the remapping surface; and
ii. remapping the pixels of the first 2D image corresponding to the points of intersection to generate the remapped image, whereby the pixels are remapped according to the direction of rays projected from the viewpoint of the second 2D image via the intersection points corresponding to each pixel,
optionally, arranged to operate in accordance with any of the methods described herein.

The invention also provides an imaging system, comprising:
a 2D imaging system arranged in use to obtain 2D images to be registered with
a 3D image data set; and
a processor, arranged in use to:
a) obtain first and second 2D images through an object to be imaged, wherein the images are from different viewpoints with respect to the object;
b) obtain a third 2D image through an object to be imaged, wherein the third image shares the viewpoint of the first image and is aligned with the first image;

c) define a remapping surface within the 3D image data set;
d) register the first and second 2D images with the 3D image data set and determining the viewpoint of the first and second 2D images with respect to the 3D image data set;
e) remap pixels of the third 2D image to generate an image from the viewpoint of the second 2D image by:
   i. determining which pixels of the third 2D image correspond to the pixels of the first 2D image;
   ii. back projecting rays from the pixels of the first 2D image and determining the points of intersection of the back projected rays with the remapping surface; and
   iii. remapping the pixels of the third 2D image that correspond with the pixels of the first 2D image to generate the remapped image, whereby the pixels are remapped according to the direction of rays projected from the viewpoint of the second 2D image via the intersection points corresponding to each pixel, optionally, arranged to operate in accordance with any of the methods described herein.

Preferably the imaging systems described above are image guided surgical systems.

Preferably the imaging systems described above are systems used in minimally invasive surgery.

Minimally invasive surgery is advantageous for the reasons set out above. However, an attendant disadvantage is that features of the anatomy may not be directly visible to a surgeon during an operation. This is particularly the case during vascular surgery where it is not possible to have a direct view within a blood vessel during a procedure. Images of anatomical features gained indirectly by technical means such as X-ray fluoroscopy are a widely used and useful tool for surgeons.

Accordingly, these systems are suitable for use in surgery, in particular vascular surgery.

Vascular surgery particularly concerns tissues that move or deform during a surgical procedure. This movement and/or deformation can by due to movement of the patient during an operation. Alternatively or in addition this movement and/or deformation can be due to pressure or force exerted on features of the anatomy, in particular blood vessels, by surgical instruments or other medical devices, in particular stents, probes and/or guide wires, during an operation.

Deformation, due to instruments for example, may occur mostly during the initial phase or phases of an operation. The present invention utilises images that are taken during the process of an operation. Consequently, the present invention is not constrained to using information that is only obtained pre-operatively. Therefore advantages of the present invention include that it can be used after the majority of intra-operation deformation has occurred and thus can produce more accurate, relevant and useful images.

The invention is now illustrated with reference to the following specific examples and the accompanying drawings which show.

As noted above in relation to FIG. 2, FIG. 2a shows that remapping a first DSA image to the second viewing direction cannot be accurately achieved using only knowledge of the relative directions of views 1 and 2.

Additional knowledge is required: information on the depth position (i.e. the distance along the ray path) of anatomical features inside the patient. In FIG. 2a, the grey circle inside the patient is projected into the detector along the dotted line using the first view direction. However, when the source is moved to the second view direction, the circle seen in view 1 cannot be directly remapped to view 2.

To perform such a remapping extra information on the grey circle's position inside the patient is required. This is because the circle seen in view 1 might be projected from any point along the blue line intersecting the patient, such as the points marked with +, which if used for remapping along the ray lines for view 2, result in multiple possible locations for the circle in view 2.

However, if all the 2D image information can be projected back to a single accurately known 2D surface, such as the one depicted in FIG. 2b, then the image can be remapped accurately for view 2. In FIG. 2b, the projected square, triangle and circle of view 1 can be correctly remapped to view 2 using the positional information provided by the remapping surface intersecting these features inside the patient.

Therefore it is possible to define a remapping surface inside the preoperative CT volume and then match this surface to the patient using 2D-3D registration during an operation or intervention. This surface is then used to remap a DSA image to a new view direction.

As the depth information becomes more three-dimensional (i.e. does not just originate from a single 2D remapping surface), and as errors arise in positioning the 2D surface, then errors arise in the remapping process. Consequently, the ability to define such a surface accurately is essential for a correct perspective projection remapping.

Using a 2D-3D Registration Algorithm to Facilitate DSA Remapping

Figure 4:
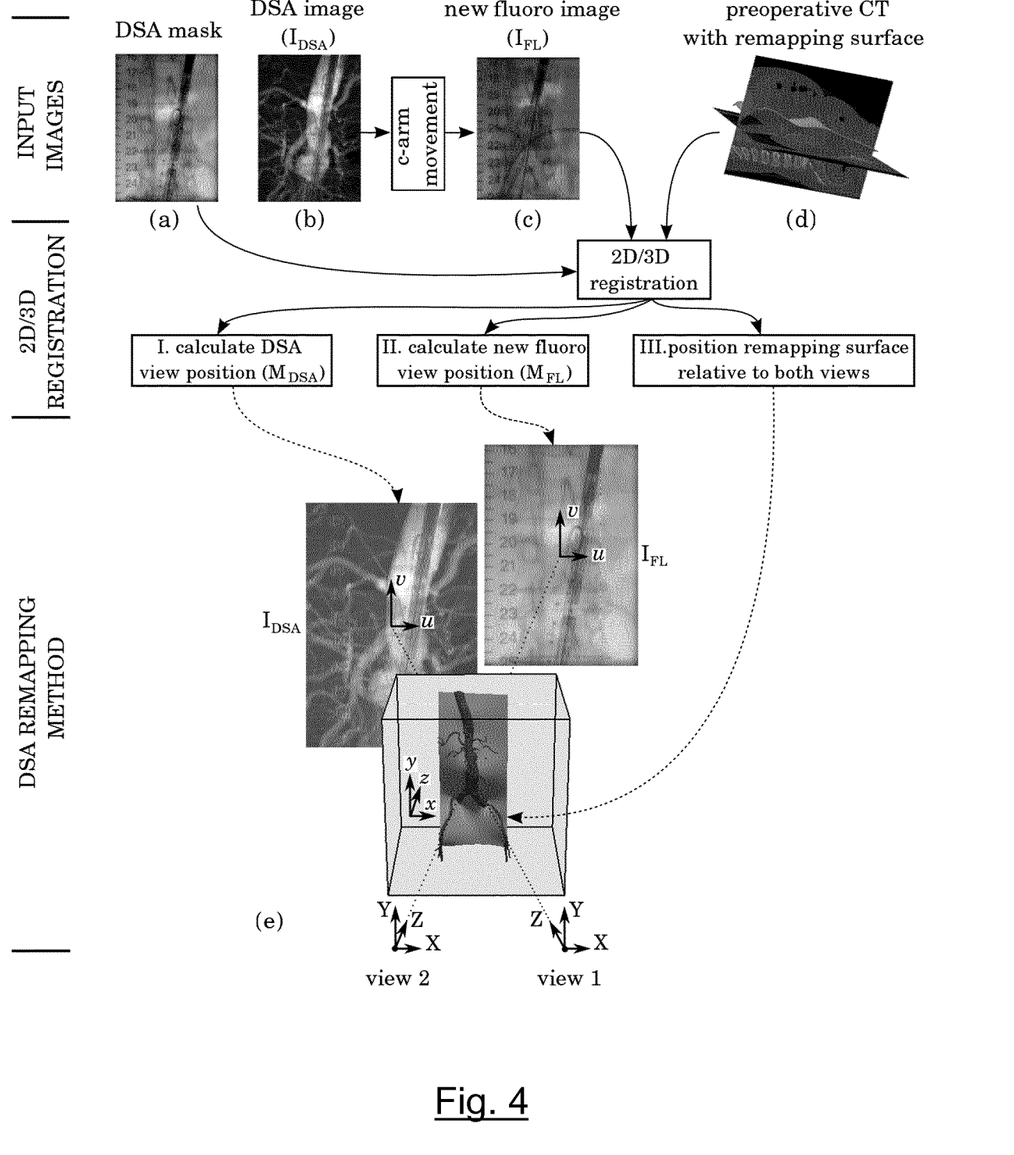
FIG. 4 Flow diagram showing how the 2D-3D registration algorithm enables DSA remapping. Input images are shown at the top: (a) DSA mask; (b) DSA image; (c) new fluoroscopy image acquired after the C-arm was moved to a new view; and (d) a preoperative CT volume comprising the remapping surface. Middle and bottom shows the 2D-3D registration which enables calculation of view directions and positioning of patient-vasculature-specific remapping surface (e).

The present disclosure utilises the 2D-3D registration algorithm noted above to facilitate DSA remapping. FIG. 4 demonstrates how the 2D-3D registration algorithm enables DSA remapping. This begins at the top with the input images: (a) a DSA mask and (b) a DSA image ($I_{DSA}$) produced from a posterior-anterior view; (c) a new fluoroscopy image ($I_{FL}$) acquired after the C-arm is moved; and (d) the preoperative CT scan with the remapping surface defined inside. Images (a), (c) and (d) are input into the 2D-3D registration algorithm which calculates the 2D-3D transformations between the CT scan $(x,y,z,1)^T$ and both the DSA image $(u,v,1)_{DSA}^T$ and the new fluoroscopy image $(u,v,1)_{FL}^T$ i.e.:

$$M_{DSA}(x,y,z,1)^T = \lambda(u,v,1)_{DSA}^T \quad (3.1)$$

$$M_{FL}(x,y,z,1)^T = \lambda(u,v,1)_{FL}^T \quad (3.2)$$

The three boxes in FIG. 4 show the subsequent stages to the 2D-3D registration which provide the necessary information to carry out DSA remapping. The Roman numerals labelling each box correspond to the following processes:

I. Calculate DSA view position: the transformation $M_{DSA}$ to position $I_{DSA}$ in relation with $CT_{3D}$ is determined using the DSA mask. Both the DSA mask and DSA image have the same transformation as they are acquired in a single angiography screening from the same view direction.

II. Calculate new fluoroscopy view position: the transformation $M_{FL}$ to position $I_{FL}$ in relation with $CT_{3D}$ is determined.

III. The transformations $M_{DSA}$ and $M_{FL}$ can position the preoperatively defined remapping surface inside the CT volume with respect to both $I_{DSA}$ and $I_{FL}$, enabling remapping to occur on a patient-vasculature-specific surface.

DSA Remapping

Figure 5:
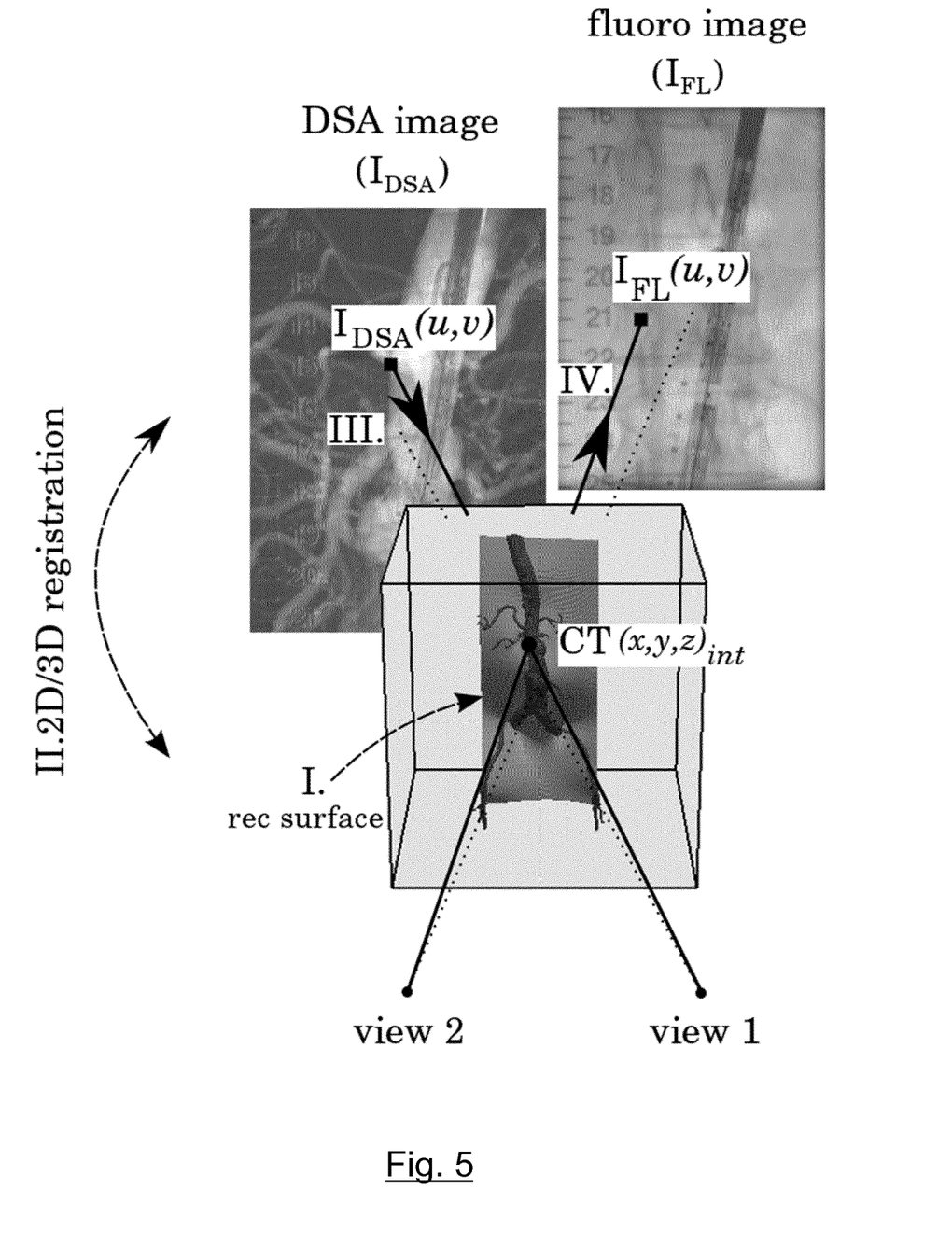
FIG. 5 DSA remapping process shown in detail for one pixel in the DSA image: $I_{DSA}(u,v)$. A ray is back projected from $I_{DSA}(u,v)$ into the remapping surface using $M_{DSA}$. The 3D interception position CT $(x,y,z)_{int}$ is then projected into the fluoroscopy image using the transformation $M_{FL}$ to acquire the 2D interception position in the fluoroscopy image $I_{FL}(u,v)$. Finally, the intensity at $I_{DSA}(u,v)$ is remapped onto $I_{FL}(u,v)$.

Thus the 2D-3D registration enables DSA remapping and is detailed in the below steps (I, II, III, IV, V) with reference to FIG. 5; the Roman numerals in FIG. 5 correspond to the following steps:

I. Segmenting a remapping surface from the preoperative CT volume. The surface should contain the blood vessels of clinical interest to be remapped.

II. Registering the CT volume with both images, $I_{DSA}$ and $I_{FL}$, using the 2D-3D registration algorithm such as that described herein. The registration allows spatial positioning of $I_{DSA}$ and $I_{FL}$ in relation to the segmented CT remapping surface as was described above with reference to boxes I and II of FIG. 4.

III. Back projecting rays from each of the DSA image pixels $I_{DSA}(u,v)$ using $M_{DSA}$, and calculating the 3D positions in $CT_{3D}$ where the rays intercept the remapping surface (i.e. CT $(x,y,z)_{int}$).

IV. Projecting rays from the 3D interception positions CT $(x,y,z)_{int}$ to $I_{FL}$ to acquire the 2D interception position in $I_{2D}$ (i.e. $I_{FL}(u,v)$). This is done using the transformation $M_{FL}$.

V. Finally, the intensity at each DSA image pixel $I_{DSA}(u,v)$ is remapped onto the 2D interception position $I_{FL}(u,v)$ corresponding to the same pixel. This automatically produces a remapped DSA image corresponding to the current fluoroscopy view.

DSA Remapping Errors

As discussed in above, remapping a projection image into a new view requires knowledge of the depth position of the anatomical features. As noted herein, such knowledge can be provided by defining a remapping surface inside the CT volume to intersect features of interest. This assumes that features lie on a single 2D surface, and that the surface can be positioned correctly. However, when these assumptions are violated three types of errors arise:

I. We define type 1 error $E_1$ to occur as a result of the thickness of the feature being remapped (i.e. feature's size along the z direction in $CT_{3D}$. $E_1$ is a function of the feature's thickness and changes in the ray paths ($\Delta rayPath$) along that feature when the C-arm is moved to a new view direction, such as:

$$E_1 = f(\text{thickness}, \Delta rayPath)$$

$$\begin{cases} E_1 = 0, \text{ if features lie completely on the remapping surface.} \\ E_1 > 0, \text{ otherwise} \end{cases}$$

When the entire feature lies on the remapping surface, then, the ray paths along that feature are similar from any view direction and $E_1$. However, when the feature's thickness increases, the changes in the ray paths increase when the C-arm is moved, and thus, $E_1$ increases as seen in FIG. 6.

Figure 6:
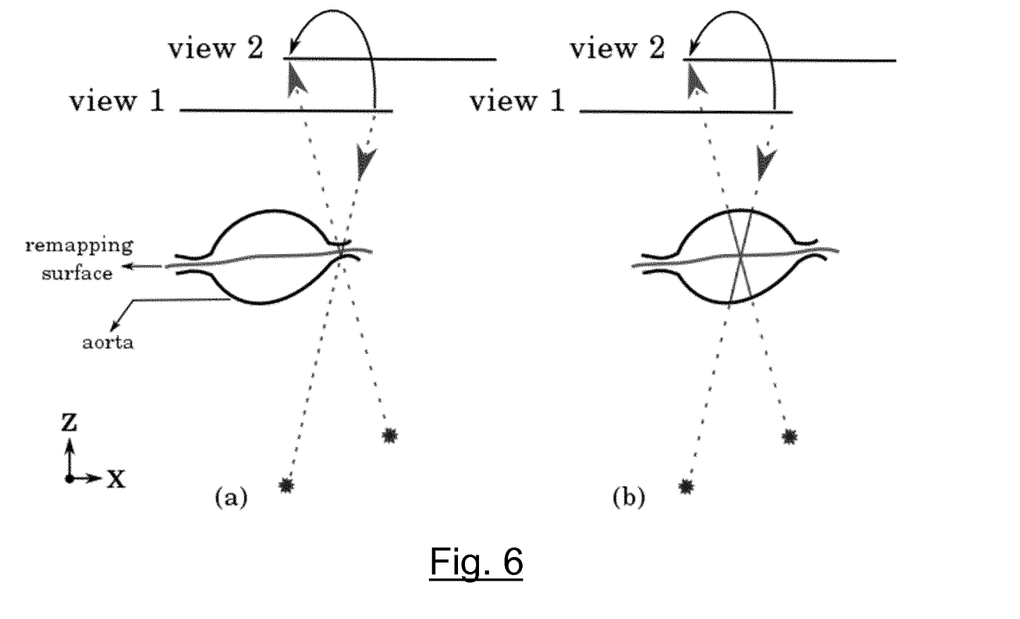
FIG. 6 DSA remapping Type 1 error $E_1$, as a function of the feature's thickness and changes in ray paths. Both (a) and (b) show images of the aorta acquired from two different views with the upward-pointing arrow intersecting a different part of the aorta than the downward-pointing arrow (indicated by solid lines), thus causing a type 1 error. In addition, (b) shows that when a feature's thickness in (b) is much larger than in (a) the solid line originating from the upward-pointing arrow is further away from the solid line originating from the downward-pointing arrow when compared to (a).

In FIGS. 6(a) and (b), two images of an aneurysmal aorta are acquired from two different view directions. In both cases, the projected ray to view 2 (upward-pointing arrow) does not intersect the same part of the aorta as the projected ray from view 1 (downward-pointing arrow). This causes type 1 error in the features' position between the remapped image from view 1 and the new image from view 2 when overlaid. In addition, in (b), the intersection of the upward-pointing arrow with the aorta (solid line) is further away from the intersection of the downward-pointing arrow (solid line) when compared to (a), this is because the feature's thickness in (b) is much larger than in (b).

II. We define type 2 error $E_2$ to be due to errors in positioning the remapping surface. $E_2$ is a function of the 2D-3D registration error ($E_{reg}$ [9]), and the intraoperative deformation ($D_{ef}$ [8]), such as:

$$E_2 = f(E_{reg}, D_{ef}) \begin{cases} E_2 = 0, \text{ if } E_{reg} = 0 \text{ and } D_{ef} = 0. \\ E_2 > 0, \text{ otherwise} \end{cases}$$

Figure 7:
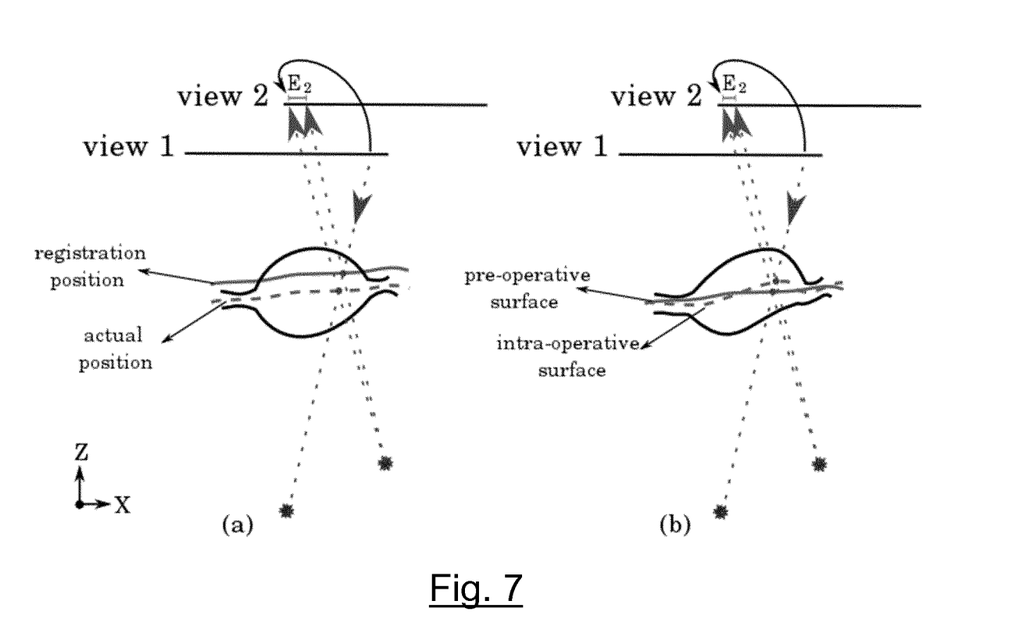
FIG. 7 DSA remapping Type 2 error $E_2$ relation with (a) the 2D-3D registration errors $E_{reg}$, and (b) the intraoperative deformation ($D_{ef}$). In both cases two images of the aorta are acquired from different views. The downward-pointing arrow intersects the CT volume at the wrong depth position causing $E_2>0$ in both (a) and (b).

$E_{reg}$ results from misaligning $CT_3D$ with $X_{3D}$ (i.e. errors in $R(\theta x, \theta y, \theta z)$ and $T(X,Y,Z)$. The translation error along the Z axis (see FIG. 3) is the largest error observed when compared to the other translation and rotation errors (5 mm vs. 0.5 mm respectively [9]). Therefore, errors in positioning the remapping surface along the Z axis may occur as shown in FIG. 7(a). In FIG. 7(a), where no deformation occurs ($D_{ef}$=0, the downward-pointing arrow intersects the CT volume at the wrong depth position because of the Z translation error causing $E_2$ error.

$D_{ef}$ is a common issue in all methods that employ preoperative anatomy for overlay. $D_{ef}$ might occur because of the movement of the stiff wires and delivery systems inside the aorta during intervention (<10 mm [8]). This might cause errors in the position of the remapping surface as illustrated in FIG. 7(b). In FIG. 7(b), where no registration error occurs $E_{reg}$, the downward-pointing arrow intersects the CT volume at the wrong depth position because of the intraoperative deformation of the remapping surface causing $E_2$ error.

III. We define type 3 error $E_3$ to be due to non-rigid movement of features of interest (relative to the vertebrae on which registration is based) between the time the DSA image $I_{DSA}$ was acquired and the time the new fluoroscopy image ($I_{FL}$) was acquired. $E_3$ is a function of the different stages during an intervention which exhibit different amounts of intraoperative deformation depending on the type of the interventional devices present.

$E_3$ is a minimum when $I_{DSA}$ and $I_{FL}$ are acquired during the same stage of the intervention as the amount of deformation should be similar for both images. However, if $I_{DSA}$ and $I_{FL}$ are acquired during different stages, then $E_3$ increases as the two images experience different amounts of deformation. In addition, the delivery device with the undeployed stent-grafts is the main cause of deformation. Therefore, if $I_{DSA}$ is acquired when the delivery device is present and $I_{FL}$ when it was not, $E_3$ is a maximum.

EXAMPLES

Experiments were carried out using data from 9 patients who underwent elective EVAR in St Thomas' hospital (London, UK). Data was processed offline, i.e. not during the procedure and was approved by the National Research Ethics Service with informed patient consent. The 2D-3D registration was performed on a computer with two NVidia GTX 690 graphic cards with each card containing two GPUs. A single 2D-3D registration was completed in 1.25 sec, and the remapping software took around 1 sec. Thus, the entire remapping process time was around 3.5 sec for each fluoroscopy image.

Each dataset had a preoperative diagnostic CT scan, acquired on a variety of machines depending on the referring hospital, with voxel sizes ranging from 0.683×0.683×0.7 mm³ to 1×1×1 mm³. Each dataset also had a number of intraoperative images (fluoroscopy screening, angiography screening and DSAs) acquired on a Siemens FP20 system with a low frame rate ranging from 2 fps to 7 fps.

Figure 8:
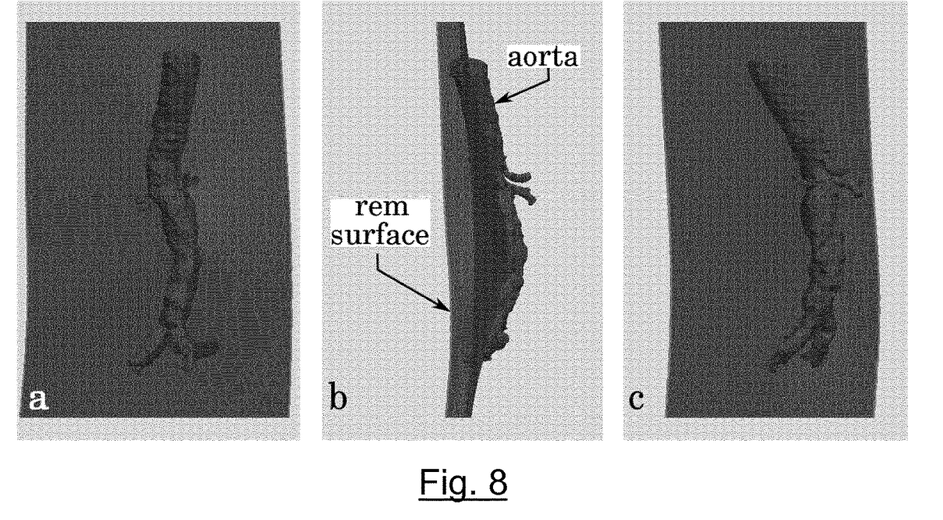
FIG. 8 A surface used for DSA remapping from different anatomical views of an aorta: (a) anterior-posterior, (b) lateral and (c) posterior-anterior. The surface is defined along the aorta using thin-plate-spline interpolation.

For each patient, the aorta was segmented from the preoperative CT volume using a semi-automatic method in ITK-SNAP [11]. The remapping surface was then defined by picking points along the midline of the aorta, iliac and renal arteries and then producing a surface using thin-plate-spline interpolation [12]. An example of such a remapping surface can be seen in FIG. 8 from different views: (a) anterior-posterior, (b) lateral and (c) posterior-anterior. This surface was chosen to remap blood vessels of interest, i.e. the aorta, and renal and iliac arteries.

For each dataset, a DSA image produced from an anterior-posterior view at an early stage of the intervention was chosen to be remapped. These DSA images show the delivery devices with the undeployed stent-grafts as well as vasculature. DSA remapping, as described herein, was then carried out to remap the chosen DSA image to a number of fluoroscopy images acquired at different stages of the intervention after C-arm movement (but approximately from anterior-posterior views).

Validation Experiments

Figure 9:
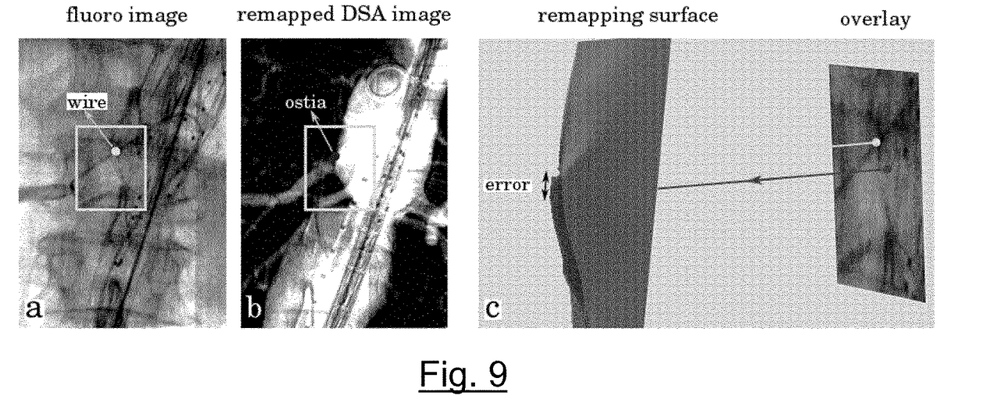
FIG. 9 Illustration of a validation method used. (a) Fluoroscopy image with a dot marking a guide-wire. (b) Remapped DSA image wherein a dot marks the renal ostium. (c) Rays are back projected from the centres of each of the dots in the overlay image into the remapping surface using the transformation $I_{FL}$, and the error is calculated in millimetres in $CT_{3D}$.

Validation images were chosen for each dataset which clearly showed the position of the renal arteries, either by the position of a guide-wire or a stent-graft, or by the use of ICM. Overlay accuracy was then calculated at a clinically relevant position: the renal ostium in both the fluoroscopy image $I_{FL}$ and the remapped DSA image $I_{DSA(rem)}$, as shown in FIG. 9. In FIG. 9, where a guide-wire is used, an error value of zero was recorded if the wire in $I_{FL}$ (light-toned dot in (a)) went through the $I_{DSA(rem)}$ renal ostium (dark-toned dot in (b)). Otherwise, the error value was calculated as described in FIG. 9(c). In FIG. 9(c), rays are back projected from the overlay image into the remapping surface using the transformation $I_{FL}$. The distance (i.e. error) between the two points of interception with the surface is then calculated in mm in $CT_{3D}$ using the formula $\sqrt{(x_1-x_2)^2+(y_1-y_2)^2+(z_1-z_2)^2}$. This method allows the error to be calculated in real anatomical distance (i.e. mm) not a projected error (i.e. pixels).

In the case where a stent-graft or an ICM was used, the middle-points of the renal ostia were located in both $I_{FL}$ and $I_{DSA(rem)}$, and the same method of back projection was used to calculate the error in millimetres. For each dataset and in all cases (i.e. wire/stent/ICM), locations of the renal ostia were located visually by two observers independently. Two sets of errors were then calculated and averaged for each dataset.

Figure 10:
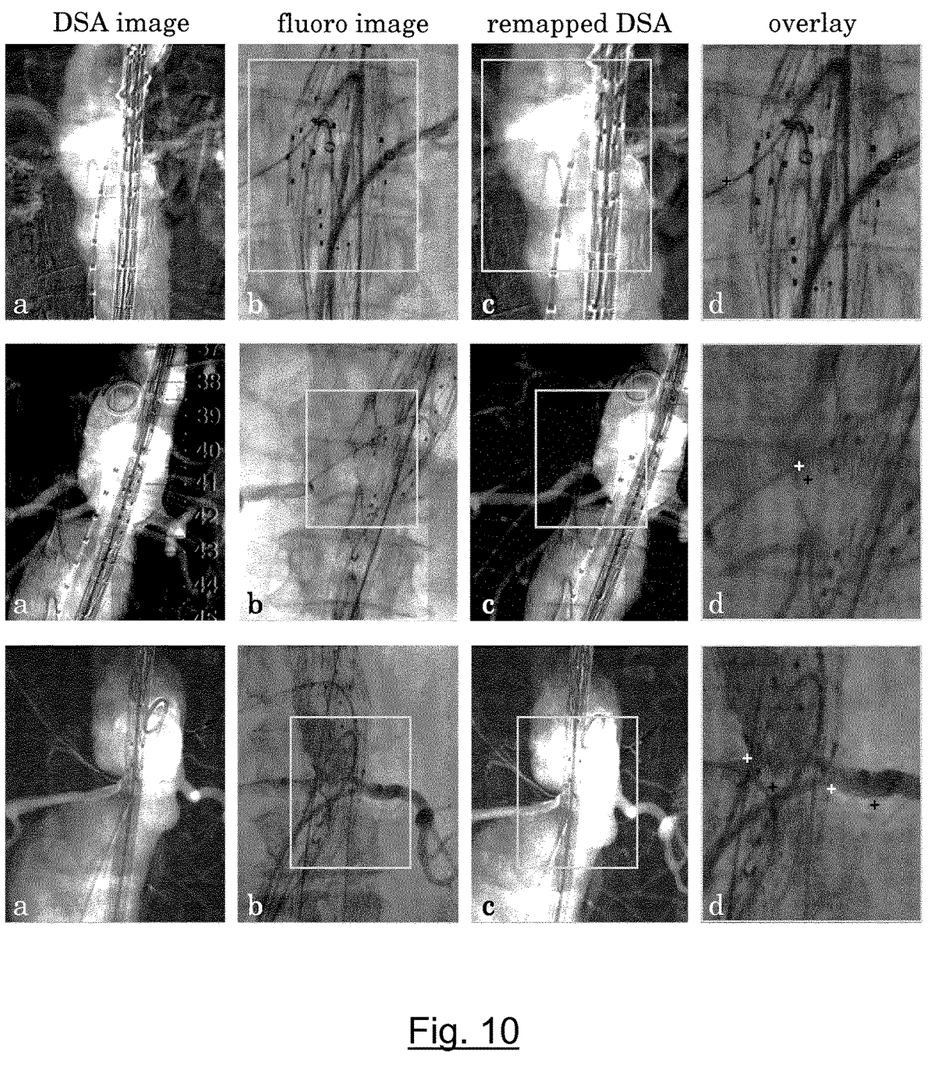
FIG. 10 Representative results from patients 2, 4 and 8 respectively. (a) $I_{DSA}$, (b) $I_{FL}$, (c) $I_{DSA(rem)}$ and (d) $I_{DSA(rem)}$ overlaid onto $I_{FL}$ in red, with the renal ostia marked with black crosses (+) in $I_{DSA(rem)}$ and white crosses (✛) in $I_{FL}$.

FIG. 10 shows results from patients 2, 4 and 8 respectively: (a) the DSA image ($I_{DSA}$); (b) the fluoroscopy image ($I_{FL}$); (c) the remapped DSA image ($I_{DSA(rem)}$; and (d) $I_{DSA(rem)}$ overlaid onto $I_{FL}$ in red, with the renal ostia marked with black crosses (+) in $I_{DSA(rem)}$ and white crosses (✣) in $I_{FL}$. Presented patients were chosen to have remapping errors which covered the full range of observed average errors: 0.82 mm, 2.92 mm and 5.52 mm, respectively.

For each patient, the remapping accuracies, as described above, were calculated for all images and averaged. Table 1 lists the number of DSA remappings for each patient, and the maximum and averaged remapping errors. The overall number of remappings performed and averaged error are also presented. Numerical results showed an overall error average of 2.50 mm over 41 remapped images, with 1 case scoring zero error and 6 other cases scoring averaged errors <3 mm. For 2 patients, larger averaged errors (>4 mm) were observed. In 5 patients, large maximum errors (>4 mm) were observed; patient 8 scored the highest maximum (11.57 mm) and averaged (5.52 mm) errors.

Results presented in Table 1 show an averaged remapping error of 2.50 mm over 41 remappings performed. Error variations across different remappings for the same patient were observed. This can be explained by the fact that remappings were performed at different stages of the procedure for each patient (as noted above). Thus, the aorta experienced different amounts of intraoperative deformation depending on the type of interventional devices present. When overlaying the segmented aorta into the remapped DSA image with the highest overlay error (i.e. 11.57 mm for patient 8), this case was found to have the biggest intraoperative deformation compared to the other DSA remappings for the same patient, which explains the larger maximum error reported for patient 8.

TABLE 1

The number of DSA remappings performed, the maximum error and the averaged remapping error in millimetres (mm) for each patient.

|  | Number of Remappings | Maximum Error (mm) | Averaged Error (mm) |
| --- | --- | --- | --- |
| Patient 1 | 5 | 3.39 | 1.79 |
| Patient 2 | 7 | 1.34 | 0.82 |
| Patient 3 | 5 | 4.41 | 2.46 |
| Patient 4 | 4 | 4.55 | 2.92 |
| Patient 5 | 3 | 0 | 0 |
| Patient 6 | 2 | 3.1 | 1.77 |
| Patient 7 | 6 | 4.64 | 2.61 |
| Patient 8 | 6 | 11.57 | 5.52 |
| Patient 9 | 3 | 6.19 | 4.58 |
| Overall | 41 | 11.57 | 2.5 |

Warping the preoperative aorta to match the intraoperative scene before segmenting the remapping surface can also be investigated by employing a non-rigid 2D-3D image registration algorithm (e.g. [13]) to account for the intraoperative deformation.

Accordingly, the invention provides methods and systems for production of 2D digital images suitable for use in medical imaging.

REFERENCES

[1] Miller, D., "Interventional fluoroscopy: reducing radiation risks for patients and staff," J. Vasc. Interv. Radiol. 20(7), 274-274 (2009).

[2] Patel, A., Gallacher, D., Dourado, R., Lyons, O., Smith, A., Zayed, H., Waltham, M., Sabharwal, T., Bell, R., Carrell, T., et al., "Occupational radiation exposure during endovascular aortic procedures," Eur. J. Vasc. Endovasc. 46(4), 424-430 (2013).

[3] McCullough, P. A., "Contrast-induced acute kidney injury," J. Am. Coll. Cardiol. 51(15), 1419-1428 (2008).

[4] Nash, K., Hafeez, A., and Hou, S., "Hospital-acquired renal insufficiency," Am. J. Kidney. Dis. 39(5), 930-936 (2002).

[5] Seeliger, E., Sendeski, M., Rihal, C. and Persson, P., "Contrast-induced kidney injury: mechanisms, risk factors, and prevention," Eur. Heart. J. 33(16), 2007-2015 (2012).

[6] Bicknell, C., "Occupational radiation exposure and the vascular interventionalist," Eur. J. Vasc. 46, 431 (2013).

[7] Markelj, P., Tomaˇeviˇz c, D., Likar, B. and Pernuˇs, F., "A review of 3D/2D registration methods for image-guided interventions," Med. Image. Anal. 16(3), 642-661 (2012).

[8] Carrell, T., Modarai, B., Brown, J. and Penney, G., "Feasibility and limitations of an automated 2D-3D rigid image registration system for complex endovascular aortic procedures," J. Endovasc. Ther. 17(4), 527-533 (2010).

[9] Penney, G., Weese, J., Little, J., Desmedt, P., Hill, D., et al., "A comparison of similarity measures for use in 2D/3D medical image registration," IEEE Trans. Med. Imag. 17(4), 586-595 (1998).

[10] Penney, G., Varnavas, A., Dastur, N. and Carrell, T., "An image-guided surgery system to aid endovascular treatment of complex aortic aneurysms: description and initial clinical experience," in [IPCAI], 6689, 13-24 (2011).

[11] Yushkevich, P. A., Piven, J., Hazlett, H. C., Smith, R. G., Ho, S., Gee, J. C. and Gerig, G., "User guided 3D active contour segmentation of anatomical structures: significantly improved efficiency and reliability," Neuroimage 31(3), 1116-1128 (2006).

[12] Rohr, K., Fornefett, M. and Stiehl, H. S., "Approximating thin-plate splines for elastic registration: Integration of landmark errors and orientation attributes," in [Inf. Process. Med. Imaging], 1613, 252-265, Springer (1999).

[13] Guyot, A., Varnavas, A., Carrell, T. and Penney, G., "Non-rigid 2D-3D registration using anisotropic error ellipsoids to account for projection uncertainties during aortic surgery," in [MICCAI], 8151, 179-186, Springer (2013).

The invention claimed is:

1. An image generation method comprising:
   a) obtaining single first and single second 2D images through an object to be imaged, wherein the images are from different viewpoints with respect to the object;
   b) providing a 3D image data set of the object to be imaged;
   c) defining a remapping surface within the 3D image data set;
   d) registering the first and second 2D images with the 3D image data set and determining a viewpoint of the first and second 2D images with respect to the 3D image data set; and
   e) remapping pixels of the first 2D image to generate a remapped 2D image from the viewpoint of the second 2D image by:
      i. back projecting rays from the pixels of the first 2D image and determining the points of intersection of the back projected rays with the remapping surface; and
      ii. remapping the pixels of the first 2D image corresponding to the points of intersection to generate the 2D remapped image, whereby the pixels of the first 2D image are remapped according to the direction of rays projected from the viewpoint of the second 2D image via the intersection points corresponding to each pixel.

2. The image generation method of claim 1, comprising:
   f) obtaining a third 2D image through an object to be imaged, wherein the third image shares the viewpoint of the first image and is aligned with the first image;
   g) providing a 3D image data set of the object to be imaged;
   h) defining a remapping surface within the 3D image data set;
   i) registering the first and second 2D images with the 3D image data set and determining the viewpoint of the first and second 2D images with respect to the 3D image data set;
   j) remapping pixels of the third 2D image to generate the remapped 2D image from the viewpoint of the second 2D image by:

i. determining which pixels of the third 2D image correspond to the pixels of the first 2D image;

ii. back projecting rays from the pixels of the first 2D image and determining the points of intersection of the back projected rays with the remapping surface; and iii. remapping the pixels of the third 2D image that correspond with the pixels of the first 2D image to generate the 2D remapped image, whereby the pixels are remapped according to the direction of rays projected from the viewpoint of the second 2D image via the intersection points corresponding to each pixel.

3. The method according to claim 1, wherein the first or second 2D image is a fluoroscopy image.

4. The method according claim 1, wherein the 3D image data set is obtained from a computerised tomography (CT) or magnetic resonance (MR) or cone beam computerised tomography (CBCT) scan.

5. The method according to claim 1, wherein the remapping surface is any of:
i. angled planar or multi-planar;
ii. curved; and/or
iii. discontinuous;
or any combination thereof.

6. The method according to claim 1, wherein the remapping surface is shaped to follow a feature of the object to be imaged.

7. The method according to claim 6, wherein the feature of the object to be imaged within the 3D image data set of the object to be imaged is enhanced by the use of contrast medium.

8. The method according to claim 1, wherein the origin of the pixels is marked.

9. The method according to claim 1 wherein the object is a patient and wherein the image generated by the remapping is used to carry out a surgical procedure on the patient.

10. The method of claim 1, further comprising administering contrast medium to the object to be imaged and thus defining a remapping surface within a 3D image data set in relation to the location of the contrast medium.

11. An imaging system, comprising:
a 2D imaging system arranged in use to obtain 2D images; and
a processor, arranged in use to:
a) obtain single first and single second 2D images through an object to be imaged, wherein the images are from different viewpoints with respect to the object;
b) obtain a 3D image data set of the object to be imaged;
c) define a remapping surface within the 3D image data set;
d) register the first and second 2D images with the 3D image data set and determine the viewpoint of the first and second 2D images with respect to the 3D image data set; and
e) remap pixels of the first 2D image to generate a remapped 2D image from a viewpoint of the second 2D image by:
i. back projecting rays from the pixels of the first 2D image and determining the points of intersection of the back projected rays with the remapping surface; and
ii. remapping the pixels of the first 2D image corresponding to the points of intersection to generate the 2D remapped image, whereby the pixels of the first 2D image are remapped according to the direction of rays projected from the viewpoint of the second 2D image via the intersection points corresponding to each pixel.

12. The imaging system according to claim 11,
wherein the 2D imaging system is arranged to obtain 2D images to be registered with a 3D image data set; and further comprising
a processor, arranged to:
f) obtain single first and single second 2D images through an object to be imaged, wherein the images are from different viewpoints with respect to the object;
g) obtain a third 2D image through an object to be imaged, wherein the third image shares the viewpoint of the first image and is aligned with the first image;
h) define a remapping surface within the 3D image data set;
i) register the first and second 2D images with the 3D image data set and determining the viewpoint of the first and second 2D images with respect to the 3D image data set;
j) remap pixels of the third 2D image to generate the remapped 2D image from the viewpoint of the second 2D image by:
i. determining which pixels of the third 2D image correspond to the pixels of the first 2D image;
ii. back projecting rays from the pixels of the first 2D image and determining the points of intersection of the back projected rays with the remapping surface; and
iii. remapping the pixels of the third 2D image that correspond with the pixels of the first 2D image to generate the 2D remapped image, whereby the pixels are remapped according to the direction of rays projected from the viewpoint of the second 2D image via the intersection points corresponding to each pixel.

* * * * *